United States Patent [19]

Hinsken

[11] Patent Number: 5,071,990

[45] Date of Patent: Dec. 10, 1991

[54] PREPARATION OF INTERMEDIATES AND THE SYNTHESIS OF N-(2-HYDROXYETHYL)-2-HYDROXYMETHYL-3,4,5-TRIHYDROXYPIPERIDINES

[75] Inventor: Werner Hinsken, Essen, Fed. Rep. of Germany

[73] Assignee: Bayer Aktiengesellschaft, Leverkusen, Fed. Rep. of Germany

[21] Appl. No.: 592,434

[22] Filed: Oct. 4, 1990

[30] Foreign Application Priority Data

Nov. 1, 1989 [DE] Fed. Rep. of Germany ....... 3936295

[51] Int. Cl.$^5$ ............................................. C07D 211/42
[52] U.S. Cl. ...................................... 546/242; 544/105
[58] Field of Search ......................... 546/242; 544/105

[56] References Cited

U.S. PATENT DOCUMENTS 3,759,929  9/1973  Klotmann et al. .................. 546/242
4,940,705  7/1990  Böshagen et al. ............... 546/133 X

FOREIGN PATENT DOCUMENTS 0000947   3/1979  European Pat. Off. .
0019899  12/1980  European Pat. Off. .
0049858   4/1982  European Pat. Off. .
0055431   7/1982  European Pat. Off. .
 344383  12/1989  European Pat. Off. .
2758025   7/1979  Fed. Rep. of Germany .
3024901   1/1982  Fed. Rep. of Germany .
3906463   7/1982  Fed. Rep. of Germany .
3611841  10/1987  Fed. Rep. of Germany .
54-106477  8/1979  Japan .
56-103163  8/1981  Japan .
62-267292 11/1987  Japan .

OTHER PUBLICATIONS

Patent Abstracts of Japan, Band 3, Nr. 128 (C–62), 24, 10/79; & JP A-54 106 477 (Nippon Shinyaku) 21-- 8-1979.
Synthesis, Nr. 10, Oct. 1987, pp. 917–919; N. Farfan et al.

Primary Examiner—Catherine S. Kilby Scalzo
Attorney, Agent, or Firm—Sprung Horn Kramer & Woods

[57] ABSTRACT

A process for the preparation of N-(2-hydroxyethyl)-2-hydroxymethyl-3,4,5-trihydroxypiperidines of the formula

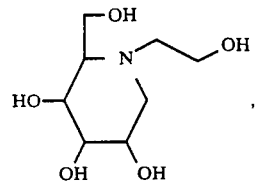

which comprises reacting a compound of the formula

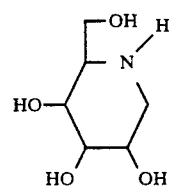

with glyoxal of the formula

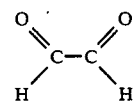

in a solvent to give the addition product

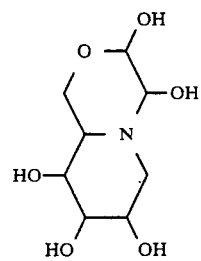

and reducing such addition product (II) with a hydrogen donor reducing agent to produce the intermediates of the formula

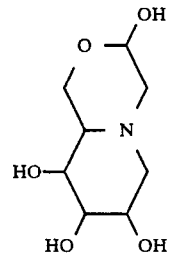

and then the end product (I).

5 Claims, No Drawings 4,071,990

PREPARATION OF INTERMEDIATES AND THE SYNTHESIS OF N-(2-HYDROXYETHYL)-2-HYDROXYMETHYL-3,4,5-TRIHYDROXYPIPERIDINES

The present invention relates to a process for the preparation of N-(2-hydroxyethyl)-2-hydroxymethyl-3,4,5-trihydroxypiperidines of the general formula (I)

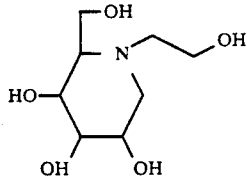

and to synthesis intermediates of the general formulae (II) and (III)

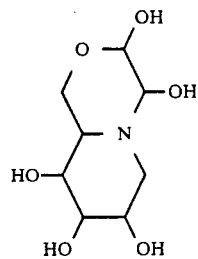

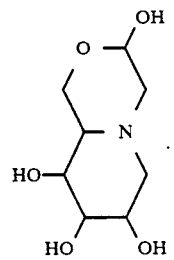

Compounds of the formula (I) are very good α-glycosidase inhibitors, in particular for disaccharidases. These compounds are thus useful agents for influencing a large number of metabolic processes.

In particular, the compound of the formula (IV) which describes the preferred stereoisomeric form of the compounds of the formula (I), can be used as an agent against diabetes (EP 947 A1).

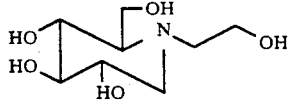

The known routes for the synthesis of the compounds of the formula (I) start from 2-hydroxymethyl-3,4,5-trihydroxypiperidines (V)

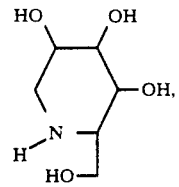

the compounds of the formula (V) being reacted with glycolaldehyde in the presence of a hydrogen donor reducing agent.

It is also known that compounds of the formula (I) are obtained when compounds of the formula (V) are reacted with ethylene oxide in a manner known per se (DE-OS (German Offenlegungsschrift) 3,024,901 A1).

All other known processes, which likewise lead to the preparation of compounds of the formula (I), are cited in European Patent Application 947 A1 and in German Offenlegungsschriften 3,024,901 A1 and 3,611,841 A.

The use of gaseous carcinogenic feed materials, expensive, poorly accessible starting components and long reaction times may be mentioned as examples of the numerous disadvantages of the processes described hitherto.

These disadvantages can be avoided by means of the process according to the invention for the preparation of compounds of the general formula (I).

The invention therefore relates to a new, chemically unique process for the preparation of N-(2-hydroxyethyl)-2-hydroxymethyl-3,4,5-trihydroxypiperidines of the formula (I), which is characterized in that compounds of the formula (V) react in a suitable solvent or solvent mixture under suitable reaction conditions with glyoxal (VI) to give the addition product (II) and are then reacted under reductive conditions with a hydrogen donor reducing agent at suitable pH values and temperatures to give the intermediate (III), and are subsequently converted by reaction with a hydrogen donor reducing agent at suitable pH values and temperatures into the target molecule (I).

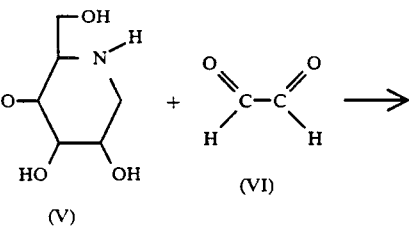

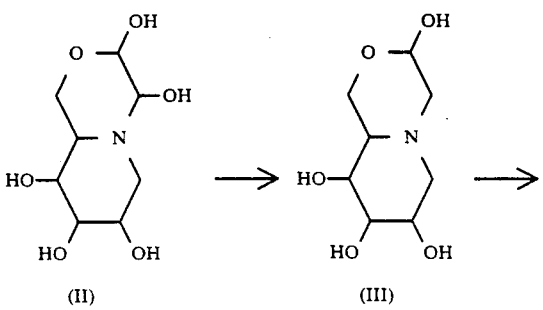

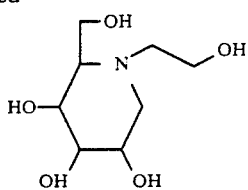

(I)

After appropriate working up, the compound (I) is obtained by crystallization from a suitable solvent or solvent mixture.

The process is also characterized in that it is possible with suitable conduct of the reaction and under suitable working-up conditions to isolate the individual reaction intermediates, the addition product (II) and the synthesis intermediate (III) which, for their part, can be used again as starting materials for further syntheses.

It has already been disclosed that both N-(2-hydroxyethyl)-N-alkylglycines are obtained [Synthesis 1987, 927] and product mixtures consisting of N,N'-dialkyl-3,3'-dioxazolidines, N-alkyl-2-oxomorpholines, N-alkyl-2,3-epoxymorpholines and N-(2-hydroxyethyl)-N-alkylglycines result [Bull. Soc. Chim. Fr. 1978 II, 83] during the reaction of N-alkylaminoethanols with glyoxal. In addition, it has also been disclosed that cyclic secondary amines react with glyoxal with the formation of 1,1,2,2-tetraaminoethanes. The formation of glycinamides has also been described (J. Heterocycl. Chem. 7, 1153 (1970)].

It is therefore to be regarded as particularly surprising that, with the reaction of 2-hydroxymethyl-3,4,5-trihydroxypiperidines (V) with glyoxal according to the invention, reaction conditions have been found which make it possible to isolate the addition product of the formula (II) as a highly pure reaction product, since with respect to the prior art it had to be expected that dioxazolidine compounds would also be formed in addition to N-alkyl-glycines and tetraaminoethane derivatives. In addition, it has been found that synthesis intermediates of the formula (III) are obtained during the reaction of compounds of the formula (II) with a hydrogen donor reducing agent in high yields after appropriate working up. Reaction conditions have also been found to convert intermediates of the formula (III) in high yields and purities by reaction with a hydrogen donor reducing agent into final products of the formula (I), which are obtained in crystalline form after suitable working up.

It is to be emphasized as an unusual feature of the reaction according to the invention that N-(2-hydroxyethyl)-2-hydroxymethyl-3,4,5-trihydroxypiperidine (I) is available in high yields and purities in a one-pot process when compounds of the formula (V) are reacted with glyoxal at temperatures between 15° and 35° C., then reduced with a hydrogen donor reducing agent at a pH between pH 4.5 and pH 8.5 and temperatures between 5° and 80° C., adjusted to a pH between pH 8.5 and pH 14 and reacted again at temperatures between 30° and 100° C. with a hydrogen donor reducing agent.

This new process for the N-hydroxyethylation of 2-hydroxymethyl-3,4,5-trihydroxypiperidines (V) thus has a number of advantages. In addition to the readily available, economical feed material, which is used, the use of highly reactive gaseous and carcinogenic feed materials which are difficult to handle is avoided. N-(2-Hydroxyethyl)-2-hydroxymethyl-3,4,5-trihydroxypiperidines (I) can thus be prepared in a substantially more economical and safer manner.

If, for example, desoxymannonojirimycin and glyoxal (30% strength solution) with water as the diluent is used as starting material in the process according to the invention, the course of the reaction can be described by the following equation.

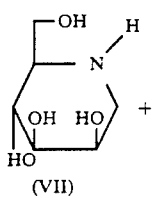

(VII)

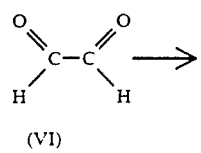

(VI)

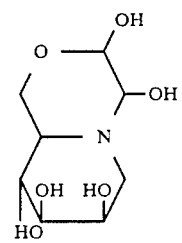

(VIII)

If sodium borohydride is added to the addition product of the formula (VIII) in aqueous medium under controlled pH as the hydrogen donor reducing agent, the following equation can be formulated.

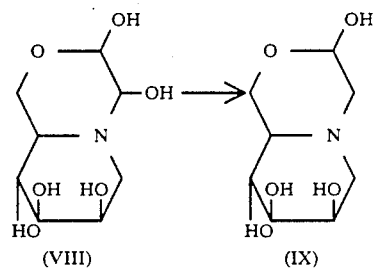

(VIII)            (IX)

If the reduction product (IX) is reacted further with sodium borohydride in basic-aqueous medium, the course of the reaction is represented by the equation below:

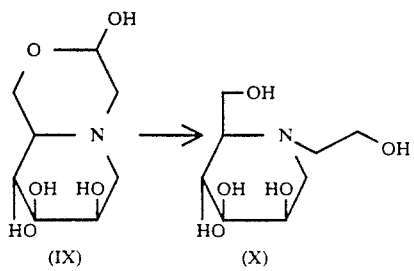

(IX)            (X)

The reaction product 1,5-didesoxy-1,5-[(2-hydroxyethyl)-imino]-D-mannitol (X) is obtained by absorption on an acidic ion exchanger and elution with aqueous ammonia solution, after concentration of the product-containing solutions and crystallization from alcohol/water.

It is irrelevant to the course of the reaction whether the individual chemical steps are carried out separately, after appropriate isolation of the reaction product, or the target molecule is isolated only after the reaction sequence in accordance with a one-pot process.

The preferred variant is the one-pot reaction, since losses in yield related to working up do not occur.

The aminosugars of the general formula (V) employed as starting material is producible by known methods [DE 3,611,841 A1, Angew. Chem. 100, 737 (1988), Carbohydr. Res. 167, 305 (1987)].

The glyoxal used as the other feed material can be used in all commercially available forms. Aqueous solutions and solid glyoxal (trimer) are preferred. 30% strength and 40% strength aqueous solutions are particularly preferred.

The preferred preparation of the addition product of the general formula (II) can be influenced by the choice of the reaction conditions, in particular the temperature. It has become evident that, in order to obtain a high yield of a highly pure reaction product (II), the reaction temperature has to be chosen such that an interval of from $+5°$ C. to $+50°$ C., preferably an interval of from $+15°$ C. to $+35°$ C., is maintained. For this purpose, a procedure can be used in which glyoxal is added as a solution or solid, optionally diluted with water or as a suspension, preferably 30% strength or 40% strength aqueous solutions, optionally with cooling, to a solution of 2-hydroxymethyl-3,4,5-trihydroxypiperidine of the general formula (V) in water or a water/alcohol mixture, where, as alcohols, those having 1 to 4 carbon atoms, preferably methanol or ethanol, or ether alcohols such as methyl glycol or ethyl glycol are used. The reaction temperature in this case should correspond to the values indicated above.

When carrying out the reaction, the ratio of the substances participating therein is widely variable. In general 1 mole of the compound of the formula (V) is reacted with 1 mole to 3 moles of glyoxal, preferably 1 mole to 2 moles, particularly preferably 1 mole to 1.5 moles of glyoxal, to prepare 1 mole of the compound of the formula (II). Compounds of the general formula (II) can be obtained in highly pure form by freeze-drying or other methods for the removal of solvents corresponding to the state of the art.

The addition compounds (II) can be converted into compounds of the general formula (III) simply by reaction with a hydrogen donor reducing agent. The reduction can in this case be carried out, on the one hand, by catalytic hydrogenation on suitable catalysts, the addition compound (II) being introduced dissolved in water or a water/alcohol mixture, or the solution obtained directly from the procedure described above can be employed. The hydrogenation is carried out on metal or noble metal catalysts, the catalyst concentration being between 0.5 mole % and 20 mole %, preferably between 0.5 mole % and 10 mole %. The hydrogen pressure and the reaction temperature can be varied within a wide range in the catalytic hydrogenation. Thus, reaction temperatures between 10° C. and 100° C. and hydrogen pressures between 10 bar and 200 bar can be chosen. Temperatures between 40° C. and 70° C. and hydrogen pressures between 30 bar and 80 bar are preferred.

On the other hand, the reaction can be carried out using complex borohydrides, which is also the preferred process variant.

In this process variant, the same aqueous or aqueous-alcoholic solutions of the addition compound (II) can be employed as described in the preceding variant. In order to obtain high yields and particularly pure compounds, it is necessary when using complex borohydrides to carry out the reaction only within a very narrow pH range from pH 4.5 to pH 8.5, advantageously pH 5.5 to pH 7.5. For this purpose, a solution or suspension of the appropriate complex borohydride is added to the aqueous or aqueous-alcoholic solution of the addition compound (II), the establishment of the desired pH, optionally with cooling, being carried out by synchronous addition of an acid and it being possible to carry out the pH measurement, for example, with a glass electrode. Suitable acids are, for example, mineral acids, preferably hydrochloric acid and sulphuric acid. The acid is preferably employed as a dilute aqueous or aqueous-alcoholic solution, concentrations of 5 to 35% by weight being possible in the case of hydrochloric acid and 5 to 90% by weight in the case of sulphuric acid.

The complex borohydrides preferably used are dialkylaminoboranes, alkali metal borohydrides and sodium cyanoborohydride. Sodium borohydride $NaBH_4$ and dimethyl-aminoborane $BH_3N(CH_3)_2$ are especially preferred. They can be added in portions or continuously as a suspension or advantageously in the form of an aqueous or aqueous-alcoholic solution. The molar ratio of addition product (II) to the reducing agent should be about 1–0.4 to 1.5, preferably 1–0.6 to 1–1.0. The reduction can be carried out at temperatures from 10° to 80° C.; temperatures between 20° and 40° C. are preferred.

After completion of the reaction, the excess of reducing agent is destroyed by addition of acid or a reactive ketone.

In order to isolate and purify the reaction product of the general formula (III), it can, depending on the process variant, be crystallized directly from the optionally concentrated batch solution or is chromatographed on suitable ion exchangers or silica gel, or else the product is absorbed on an acidic ion exchanger, eluted with optionally diluted ammonia or amine solution, and the product-containing fraction is concentrated and the residue is recrystallized from suitable solvents.

Similarly to the compounds of the formula (III), the target molecules of the formula (I) are producible by reduction with a hydrogen donor reducing agent. For this purpose, aqueous or aqueous-alcoholic solutions of the compounds (III) can be employed and also the solutions obtained from the reduction described above.

In order to achieve a sufficient reaction rate, the choice of the pH during the reaction is significant. A pH range from pH 8.5 to pH 14, advantageously pH 9 to pH 11, is to be chosen both in the catalytic hydrogenation and in the reduction with complex borohydrides.

All hydroxides and carbonates can be used as bases for pH adjustment, if they are sufficiently soluble in water and in aqueous-alcoholic mixtures. They can be employed both in solid form and in solution, the use concentration to be chosen being arbitrary.

In the catalytic hydrogenation, the reaction is carried out after the pH adjustment with the addition of metal or noble metal catalysts having a catalyst concentration between 0.1 mole % and 20 mole %, preferably between 0.4 mole % and 10 mole %.

The reaction temperature in this case is between 20° C. and 150° C., preferably between 50° C. and 90° C., at a hydrogen pressure between 10 bar and 250 bar, preferably between 40 bar and 80 bar.

The aqueous or aqueous-alcoholic solution of the compounds (III) obtained or prepared can also be converted into the target molecules (I) using complex borohydrides, which is the preferred process variant.

For this purpose, a solution or suspension of the appropriate complex borohydride is added to the aqueous or aqueous-alcoholic solution of the compound (III) after the adjustment of the pH, it being possible to carry out the addition in portions or continuously as a suspension or, advantageously, in the form of an aqueous or aqueous-alcoholic solution, optionally with cooling. The molar ratio of compounds of the formula (III) to the reducing agent should be about 1-0.4 to 1.5, preferably 1-0.6 to 1-1.0. The reduction can be carried out at temperatures from 20° C. to 90° C.; temperatures between 40° C. and 70° C. are preferred. The complex borohydrides used are preferably alkali metal borohydrides and dialkylaminoboranes. Sodium borohydride NaBH$_4$ is especially preferred.

After completion of the reaction, the excess of reducing agent is destroyed by addition of acid or a reactive ketone.

In order to isolate and purify the target molecule (I), the product is chromatographed on suitable ion exchangers or silica gel or else absorbed on an acidic ion exchanger, eluted with optionally diluted ammonia or amine solution, and the product-containing fractions are concentrated and the residue is recrystallized from suitable solvents.

Acidic ion exchangers which can be used are in principle all weakly and strongly acidic types. They can be both gel-form and macroporous.

EXAMPLE 1

(7S, 8R, 9R, 9aR)-3,4,7,8,9-Pentahydroxy-octahydropyrido-[2,1-c][1,4]oxazine

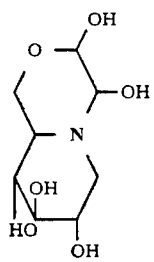

7.7 ml of 40% strength aqueous glyoxal solution are added at room temperature to a solution of 10 g of 1,5-didesoxy-1,5-amino-D-glucitol in 20 ml of deionized water and the mixture is stirred at this temperature for 30 minutes. The solution is frozen and the solvent is removed by means of freeze-drying. The crystals are ground with a mortar and pestle, suspended in a little diisopropyl ether and stirred at room temperature for about 30 minutes. The product is isolated by filtration.

Yield: 13 g (95.8% of theory)

Mass spectrum:

The most important peak in the upper mass range is at m/e=203 (M-H$_2$O).

The substance is a mixture of diastereomeric compounds.

EXAMPLE 2

(7S, 8R, 9S, 9aR)-3,4,7,8,9-Pentahydroxy-octahydropyrido-[2,1-c][1,4]oxazine

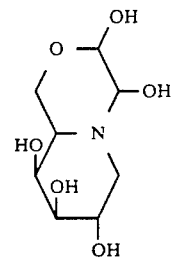

Preparation is carried out analogously to Example 1 from 1,5-didesoxy-1,5-imino-D-galactitol and corresponding molar ratios of 30% strength aqueous glyoxal.

Yield: 12.8 g (94% of theory)

C$_8$H$_{15}$NO$_6$ (221.2)

Calc.: C 43.4% H 6.8% N 6.3%

Found: C 43.2% H 6.6% N 6.5%.

EXAMPLE 3

(7S, 8R, 9S, 9aR)-3,7,8,9-Tetrahydroxy-octahydropyrido-2,1-c][1,4]oxazine

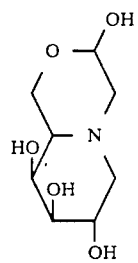

Method A:

50 g of the compound from Example 2 are dissolved in 400 ml of deionized water and 4 g of 10% strength Pd/C are added. The mixture is hydrogenated at 60° C. and a hydrogen pressure of 50 bar, the course of the reaction being followed by means of HPLC. The catalyst is filtered off with suction from contact with the solution, which is concentrated and the residue recrystallized from isopropanol/deionized water.

Yield: 34.8 g (75.2% of theory)

Method B:

50 g of the compound from Example 2 are dissolved in 350 ml of deionized water. A pH value of pH 5 to pH 5.5 is established using 15% strength sulphuric acid. A solution of 7.0 g of sodium borohydride in 30 ml of deionized water is then added to the reaction mixture continuously. The pH value is kept between pH 6.5 and pH 7.1 by dropwise addition of 15% strength sulphuric acid, and the temperature at 20° to 35° C. by cooling. The mixture is subsequently stirred for 30 minutes and the crude solution is then washed through an acidic ion exchanger in the H$^{\oplus}$ form. The exchanger is washed with deionized water and then eluted with 5% strength ammonia solution. The product fractions are concentrated and the residue is recrystallized from isopropanol/deionized water.

Yield: 39.5 g (85.3% of theory).

Mass spectrum:

The most important peaks in the upper mass range are at m/e=205 and m/e=188. Other peaks are found at m/e=146, m/e=55.

The substance is a mixture of two diastereomeric compounds.

Taking into consideration the molar ratios, the solutions obtained in Example 2 after the stirring time can be employed directly for the reaction according to method A or method B.

EXAMPLE 4

(7S, 8R, 9R, 9aR)-3,7,8,9-Tetrahydroxy-octahydropyrido-[2,1-c][l,4]oxazine

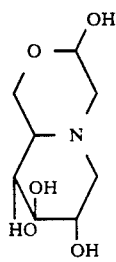

The preparation is carried out analogously to Example 3 from 50 g of the compound from Example 1 and the feed materials in each case indicated in the different methods.

Yield:
Method A: 35.4 g (76.4% of theory).
Method B: 39.3 g (84.6% of theory).
$C_8H_{15}NO_5$ (205.2):
Cal.: C 46.8% H 7.4% N 6.8%;
Found: C 46.6% H 7.6% N 6.9%.

The substance is a mixture of two diastereomeric compounds.

Taking into consideration the molar ratios, the solutions obtained in Example 1 after the stirring time can be employed directly for the reaction according to method A or method B.

EXAMPLE 5

Preparation of 1,5-didesoxy-1,5-[(2-hydroxyethyl)-imino]-D-glucitol

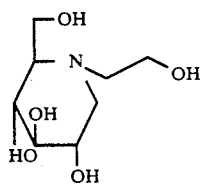

Method A:

100 g of the compound from Example 4 are dissolved in 600 ml of deionized water and a pH value of pH is established using 45% strength sodium hydroxide solution. A solution of 12 g of sodium borohydride in 50 ml of deionized water is added dropwise at room temperature. The temperature is allowed to come to 50° C. and this temperature is maintained. The course of the reaction is followed by means of HPLC. After completion of the reaction, the mixture is adjusted to pH 7 with 15% strength sulphuric acid and the crude solution is poured through an acidic ion exchanger in the H⊕ form. The exchanger is washed with deionized water and then eluted with 6% strength ammonia solution. The product fractions are concentrated and the residue is recrystallized from ethanol/deionized water.

Yield: 84.3 g (83.6% of theory)

Method B (one-pot process):

100 g of 1,5-didesoxy-1,5-imino-D-glucitol are dissolved in 200 ml of deionized water and 91 ml of glyoxal (40% strength) are added at room temperature. The mixture is subsequently stirred for 30 minutes, adjusted to pH 5 to pH 5.5 with 10% strength hydrochloric acid and a solution of 14 g of sodium borohydride in 50 ml of deionized water is added. The pH is kept between pH 6.5 and pH 7.1 by dropwise addition of 10% strength hydrochloric acid, and the temperature is kept between 20° and 40° C. by cooling. 30 minutes after addition is complete, a pH of 9 is established at 20° C. 30% strength sodium hydroxide solution and then a solution of 17.4 g of sodium borohydride in 80 ml of deionized water is added. The temperature is allowed to come to 50° C. and this temperature is maintained. The course of the reaction is followed by means of HPLC. After completion of the reaction, the mixture is adjusted to pH 7 with 10% strength hydrochloric acid and the crude solution is poured through an acidic ion exchanger in the H⊕ form. The exchanger is washed with deionized water and then eluted with 6% strength ammonia solution. The product fractions are concentrated and the residue is recrystallized from ethanol/deionized water.

Yield: 109.7 g (86.3% of theory)

M.p.: 145°–147° C.

EXAMPLE 6

Preparation of 1,5-didesoxy-1,5-[(2-hydroxyethyl)-imino]-D-galactitol

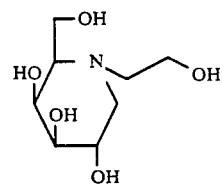

The preparation is carried out analogously to Example 5 in accordance with method A from 100 g of the compound from Example 3 and the feed materials indicated in method A.

Yield: 81 1 g (80.3% of theory)

or in accordance with method B from 100 g of 1,5-didesoxy-1,5-imino-D-galactitol and the feed materials indicated in method B.

Yield: 104.8 g (82.5% of theory).

Mass spectrum:

The most important peak in the upper mass range is at m/e=176 (M—CH$_2$OH).

It will be understood that the specification and examples are illustrative but not limitative of the present invention and that other embodiments within the spirit and scope of the invention will suggest themselves to those skilled in the art.

I claim:

1. A process for the preparation of N-(2-hydroxyethyl)-2-hydroxymethyl-3,4,5-trihydroxypiperidines of the formula

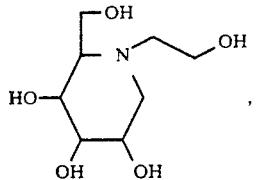  (I)

which comprises reacting a compound of the formula

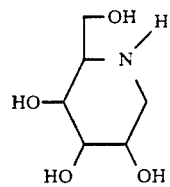  (V)

with glyoxal of the formula

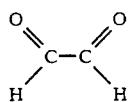  (VI)

in a solvent to give the addition product

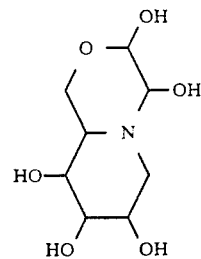  (II)

and reducing such addition product (II) with a hydrogen donor reducing agent to produce the intermediates of the formula

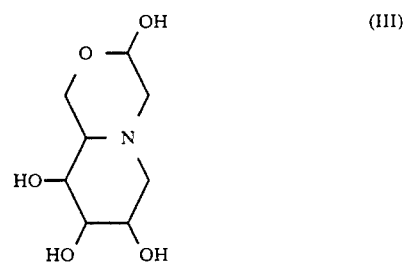  (III)

and then the end product (I).

2. The process according to claim 1, wherein the compound (II) is (7S, 8R, 9R, 9aR)-3,4,7,8,9-pentahydroxy-octahydropyrido[2,1-c][1,4]oxazine.

3. The process according to claim 1, wherein the compound (II) is (7S, 8R, 9S, 9aR)-3,4,7,8,9-pentahydroxy-octahydropyrido[2,1-c][1,4]oxazine.

4. The process according to claim 1, wherein the compound (II) is (7S, 8R, 9S, 9aR)-3,7,8,9-tetrahydroxy-octahydropyrido[2,1-c][1,4]oxazine.

5. The process according to claim 1, wherein the compound (III) is (7S, 8R, 9R, 9aR)-3,7,8,9-tetrahydroxy-octahydropyrido[2,1-c][1,4]oxazine.

* * * * *